(12) United States Patent
Cordemans De Meulenaer et al.

(10) Patent No.: US 7,632,413 B2
(45) Date of Patent: Dec. 15, 2009

(54) PROCESS FOR TREATING A LIQUID MEDIUM USING ULTRASOUND

(75) Inventors: Eric D. Cordemans De Meulenaer, Wezembeek (BE); Baudouin Hannecart, Uccle (BE); Yves Canivet, Ciney (BE)

(73) Assignee: Ashland Licensing and Intellectual Property LLC, Dublin, OH (US)

( * ) Notice: Subject to any disclaimer, the term of this patent is extended or adjusted under 35 U.S.C. 154(b) by 76 days.

(21) Appl. No.: 10/533,679

(22) PCT Filed: Nov. 4, 2003

(86) PCT No.: PCT/US03/35029

§ 371 (c)(1),
(2), (4) Date: Apr. 2, 2007

(87) PCT Pub. No.: WO2004/041314

PCT Pub. Date: May 21, 2004

(65) Prior Publication Data

US 2008/0056937 A1 Mar. 6, 2008

Related U.S. Application Data

(63) Continuation-in-part of application No. 10/358,445, filed on Feb. 4, 2003, now Pat. No. 6,736,979.

(60) Provisional application No. 60/423,368, filed on Nov. 4, 2002.

(51) Int. Cl.
*A61L 2/025* (2006.01)

(52) U.S. Cl. ............. 210/748; 210/758; 210/764; 422/20; 422/22; 604/5.02

(58) Field of Classification Search ............... 210/748
See application file for complete search history.

(56) References Cited

U.S. PATENT DOCUMENTS

| 2,163,649 A | 6/1939 | Weaver |
| 2,717,874 A | 9/1955 | Verain |
| 3,634,243 A | 1/1972 | Wessels et al. |
| 3,672,823 A | 6/1972 | Boucher |
| 4,003,832 A | 1/1977 | Henderson et al. |
| 4,076,617 A | 2/1978 | Bybel et al. |
| 4,144,722 A | 3/1979 | Mattwell |

(Continued)

FOREIGN PATENT DOCUMENTS

DE 44 07 564 9/1995

(Continued)

OTHER PUBLICATIONS

Böhm et al., "Viability of plant cell suspensions exposed to homogeneous ultrasonic fields of different energy density and wave type," Ultrasonics, vol. 38, pp. 629-632 (2000).

(Continued)

*Primary Examiner*—Peter A Hruskoci
(74) *Attorney, Agent, or Firm*—Knobbe, Martens, Olson & Bear LLP

(57) ABSTRACT

Devices and methods for treating, preventing from growth, and neutralizing hyperproliferative, undifferentiated, or virally infected cells in a liquid medium using high-frequency, low-energy ultrasound.

12 Claims, 8 Drawing Sheets

U.S. PATENT DOCUMENTS

| | | | |
|---|---|---|---|
| 4,211,744 A | 7/1980 | Boucher | |
| 4,294,853 A | 10/1981 | Williams et al. | |
| 4,514,149 A | 4/1985 | Kanebako et al. | |
| 4,602,184 A | 7/1986 | Meitzler | |
| 4,605,507 A | 8/1986 | Windgassen et al. | |
| 4,820,260 A | 4/1989 | Hayden | |
| 4,879,045 A | 11/1989 | Eggerichs | |
| 4,961,860 A | 10/1990 | Masri | |
| 4,971,991 A | 11/1990 | Umemura et al. | |
| 4,975,109 A | 12/1990 | Friedman, Jr. et al. | |
| 5,130,031 A | 7/1992 | Johnston | |
| 5,130,032 A | 7/1992 | Sartori | |
| 5,145,981 A | 9/1992 | Willingham | |
| 5,198,122 A | 3/1993 | Koszalka et al. | |
| 5,215,680 A | 6/1993 | D'Arrigo | |
| 5,224,051 A | 6/1993 | Johnson | |
| 5,256,182 A | 10/1993 | Friedman, Jr. et al. | |
| 5,380,411 A | 1/1995 | Schlief | |
| 5,401,237 A | 3/1995 | Tachibana et al. | |
| 5,416,210 A | 5/1995 | Sherba et al. | |
| 5,534,172 A | 7/1996 | Perry et al. | |
| 5,558,092 A | 9/1996 | Unger et al. | |
| 5,593,596 A | 1/1997 | Bratten | |
| 5,611,993 A | 3/1997 | Babaev | |
| 5,616,544 A | 4/1997 | Kalota et al. | |
| 5,632,886 A | 5/1997 | Staniec | |
| 5,827,204 A | 10/1998 | Grandia et al. | |
| 5,997,812 A | 12/1999 | Burnham et al. | |
| 6,068,857 A | 5/2000 | Weitschies et al. | |
| 6,077,431 A | 6/2000 | Kawanishi et al. | |
| RE36,939 E | 10/2000 | Tachibana et al. | |
| 6,221,814 B1 | 4/2001 | Kaburagi et al. | |
| 6,242,391 B1 | 6/2001 | Fukutani et al. | |
| 6,258,759 B1 | 7/2001 | Futahashi et al. | |
| 6,308,714 B1 | 10/2001 | Peterson et al. | |
| 6,309,355 B1 | 10/2001 | Cain et al. | |
| 6,322,749 B1 | 11/2001 | McCarthy et al. | |
| 6,342,522 B1 | 1/2002 | Mason et al. | |
| 6,413,216 B1 | 7/2002 | Cain et al. | |
| 6,428,532 B1 | 8/2002 | Doukas et al. | |
| 6,447,720 B1 | 9/2002 | Horton et al. | |
| 6,450,738 B1 | 9/2002 | Ripley | |
| 6,518,225 B1 | 2/2003 | Fukutani et al. | |
| 6,540,922 B1 | 4/2003 | Cordemans et al. | |
| 6,656,436 B1 | 12/2003 | Sentagnes et al. | |
| 6,736,979 B2 | 5/2004 | de Meulenaer et al. | |
| 6,770,248 B2 | 8/2004 | Haggett et al. | |
| 7,048,863 B2 * | 5/2006 | Swinnen et al. | 210/748 |
| 7,267,778 B2 * | 9/2007 | de Meulenaer et al. | 210/695 |
| 7,404,906 B2 * | 7/2008 | Swinnen et al. | 210/748 |
| 7,448,859 B2 * | 11/2008 | de Meulenaer et al. | 425/28.1 |
| 7,514,009 B2 * | 4/2009 | Swinnen et al. | 210/748 |
| 2001/0002251 A1 | 5/2001 | Woodburn et al. | |
| 2002/0111569 A1 | 8/2002 | Rosenschein et al. | |
| 2003/0132165 A1 | 7/2003 | de Meulenaer et al. | |
| 2003/0136824 A1 | 7/2003 | Simon | |

FOREIGN PATENT DOCUMENTS

| | | |
|---|---|---|
| DE | 44 30 587 | 2/1996 |
| DE | 19700164 | 7/1998 |
| EP | 0 577 871 | 1/1994 |
| EP | 0 619 104 | 10/1994 |
| EP | 0 633 049 | 9/1995 |
| EP | 0 680 779 | 11/1995 |
| EP | 0 515 346 | 2/1996 |
| EP | 0 661 090 | 6/1998 |
| EP | 0936187 | 8/1999 |
| EP | 1008556 | 6/2000 |
| GB | 1389291 | 4/1975 |
| JP | 5-8128113 | 7/1983 |
| JP | 5-228480 | 9/1993 |
| JP | 5-228481 | 9/1993 |
| JP | 5-228496 | 9/1993 |
| JP | 5-345192 | 12/1993 |
| JP | 7-155756 | 6/1995 |
| WO | WO 80/00226 | 2/1980 |
| WO | WO 93/13674 | 7/1993 |
| WO | WO 98/01394 | 1/1998 |
| WO | WO 00/02821 | 1/2000 |
| WO | WO 2004/041314 | 5/2004 |
| WO | WO 2005/005322 | 1/2005 |

OTHER PUBLICATIONS

Miller, Douglas L., "Effects of a High-Amplitude 1-MHz Standing Ultrasonic Field on the Algae Hydrodictyon," IEEE Transaction on Ultrasonics, Ferroelectrics, and Frequency Control, vol. UFFC-33. No. 2, pp. 165-170, Mar. (1986).

Pétrier et al., "Sonochemical Degradation of Phenol in Dilute Aqueous Solutions: Comparison of the Reaction Rates at 20 and 487 kHz," J. Phys. Chem. vol. 98, No. 41, pp. 10514-10520 (1994).

Umemura et al., "Sonodynamic treatment by inducing microbubble reaction," J.E.M.U. vol. 19, No. 2/3, pp. 266-270 (1998).

Umemura, et al., "Mechanism of Cell Damage by Ultrasound in Combination with Hematoporphyrin," Jpn. J. Cancer Res., vol. 81, pp. 962-966, (Sep. 1990).

Vollmer, et al., "Bacterial stress responses to 1-Megahertz pulsed ultrasound in the presence of microbubbles," Applied and Environmental Microbiology, pp. 3927-3931, (Oct. 1998).

Yu et al., "A review of research into the uses of low level ultrasound in cancer therapy," Ultrasonics Sonochemistry, vol. 11, pp. 95-103 (2004).

Hua I et al., "Optimization of Ultrasonic Irradiation as an Advanced Oxidation Technology," Environ. Sci. Technol. vol. 31, No. 8, pp. 2237-2243, Aug. 1997.

Marmor, et al., "Tumor eradication and cell survival after localized hyperthermia induced by ultrasound," Cancer Research, vol. 39, pp. 2166-2171, (Jun. 1979).

Miller, et al., "Single strand DNA breaks in human leukocytes inducted by ultrasound in vitro," Ultrasound in Med. & Biol., vol. 15, No. 8, pp. 765-771, (1989).

Nyborg, W. L. and Ziskin, M. C. (Eds.), *Biological Effects of Ultrasound*, Churchill-Livingstone Inc., New York, pp. 23-33, (1985).

Phull S. S. et al., "The Development and Evaluation of Ultrasound in the Biocidal Treatment of Water," Ultrasonics Sonochemistry, vol. 4, No. 2, pp. 157-164, Apr. 1997.

Wyllie, et al., "Apoptosis and the regulation of cell numbers in normal and neoplastic tissues: an overview," Cancer and Metastasis Reviews, vol. 11, pp. 95-103, (1992).

European Search Report for PCT/US2004/021664 Dated Jan. 9, 2006.

* cited by examiner

PROCESS FOR TREATING A LIQUID MEDIUM USING ULTRASOUND

CROSS-REFERENCE TO RELATED APPLICATIONS

The present application is a U.S. National Phase under 35 U.S.C. § 371 of PCT Application No. PCT/US03/35029, filed Nov. 4, 2003, which claims priority under 35 U.S.C. § 119(e) to U.S. Provisional Application No. 60/423,368, filed Nov. 4, 2002, and which is a continuation-in-part of U.S. application Ser. No. 10/358,445, filed Feb. 4, 2003, now U.S. Pat. No. 6,736,979.

FIELD

The present invention is directed to using high-frequency, low-energy ultrasound to treat liquid mediums. In specific embodiments the devices and methods herein can induce significant apoptosis in cells suspended in a physiological fluid.

BACKGROUND

Cells can be damaged by exposure to ultrasound. For example, ultrasound can cause irreversible cell damage and induce destructive cell membrane modifications. Several reports have suggested that cavitation resulting from the collapse of gas bubbles generated by acoustic pressure fields may be the cause for cell damage following ultrasonic irradiation. It has also been suggested that cavitation induces single-strand breaks in DNA by the action of residual hydrogen peroxide.

The use of ultrasound in cancer therapy has become an important issue. Ultrasound has been used in conjunction with hyperthermia, and photo-, radio-, and chemotherapy. Malignant cells are known to be more susceptible to these combined methods than their normal counterparts. The effect of direct irradiation (e.g., ultrasound, laser, light) on certain molecules (e.g., classical photosensitizers and sonosensitizers) is the generation of highly active oxygen species such as singlet oxygen, superoxide radicals, hydroperoxides, or fatty acid radicals, which can play an important role in cancer treatment, acting selectively on malignant cells.

According to the origin of the radiation, the above-described therapy is termed PDT (photodynamic therapy) or, if by ultrasound or sonoluminescence: SDT (sonodynamic therapy). Addition of a photosensitizer is a pre-requisite for both therapies. While the general effects induced by SDT and PDT are different in terms of cell viability, both SDT (specifically related to the ultrasonic cavitational activity) and PDT generate active oxygenated species and lead to a diminution of the intracellular thiol levels. In the case of PDT by ultraviolet-A (UVA), apoptosis of T helper cells can be induced by the generation of singlet oxygen, but this effect depends essentially on the initial concentration in photosensitizers (PS) and on the local oxygen concentration. For SDT, as a result of the high energies involved, the cell lysis is the major phenomenon, probably masking other effects on the surviving cells.

U.S. Pat. No. 4,971,991 to Umemura et al. discloses the use of ultrasound to treat tumor cells, but relies on high ultrasound power levels, and does not describe the use of microbubbles. Other patents describing ultrasound and microbubbles, such as U.S. Pat. No. 5,215,680 to D'Arrigo, rely on the use of the cavitational and thermal effects of ultrasound to treat tumors, as opposed to individual cancer cells, the extent of which is determined by duration and number of treatments. This type of treatment uses high power and long irradiation times, predominantly producing cell lysis and necrosis. See Kondo, *Cancer Letters* 178(1), 63-70, (2002).

DETAILED DESCRIPTION

Apoptosis, or programmed cell death, is a normal component of the development and health of multicellular organisms. Apoptosis ensures the homeostasis of tissues during development, host defense, aging, and occurs in response to a large variety of signals including γ-irradiation and ultraviolet exposure. Cells die in response to a variety of stimuli, typically during apoptosis they do so in a controlled fashion. This makes apoptosis distinct from another form of cell death called necrosis in which uncontrolled cell death leads to lysis of cells, inflammatory responses and, potentially, to serious health problems. Apoptosis, by contrast, is a process in which cells play an active role in their own death, which is why apoptosis is often referred to as cell suicide.

Upon receiving specific signals instructing the cells to undergo apoptosis, a number of distinctive biochemical and morphological changes typically occur in the cell. For example, a family of proteins known as caspases are typically activated in the early stages of apoptosis. These proteins breakdown or cleave key cellular substrates that are required for normal cellular function, including structural proteins in the cytoskeleton and nuclear proteins such as DNA repair enzymes. Caspases can also activate other degradative enzymes such as DNases, which cleave the DNA in the nucleus. In general, apoptotic cell death is characterized by early changes in the nuclear membrane, chromatin condensation, and DNA fragmentation. These biochemical changes result in morphological changes in the cell.

The teachings herein are directed towards devices and methods which can neutralize, prevent the growth of, and remove hyperproliferative cells (e.g., tumor cells) present in a liquid medium. In more specific embodiments, the methods and devices provided herein induce apoptosis in hyperproliferative cells present in a suspension, such as a physiological fluid. Treatable physiological fluids include blood, plasma, serum, and cerebrospinal fluid which can be extracted from and/or administered to animals, including mammals, humans, and the like.

Low-energy, high-frequency ultrasonic treatment according to the teachings herein can induce apoptotic effects in hyperproliferative cells. These effects include for example, having an effect on mitochondrial membranes (drop of mitochondrial potential), loss of phosphatidylserine asymmetry, provoking a lipidic oxidation of the membrane (decrease of cellular GSH level), morphological variations, DNA fragmentation, loss of plasma membrane, and the like. Furthermore, low-energy ultrasound-induced apoptosis can involve activation of caspase-3, the proteolytic degradation of the caspase substrate PARP, and the modulation of bcl-2/bax ratio in the cells.

Specific tests (see Examples) have confirmed the very rapid induction of apoptosis with limited amounts of necrosis.

Devices and Methods

Figure 1:
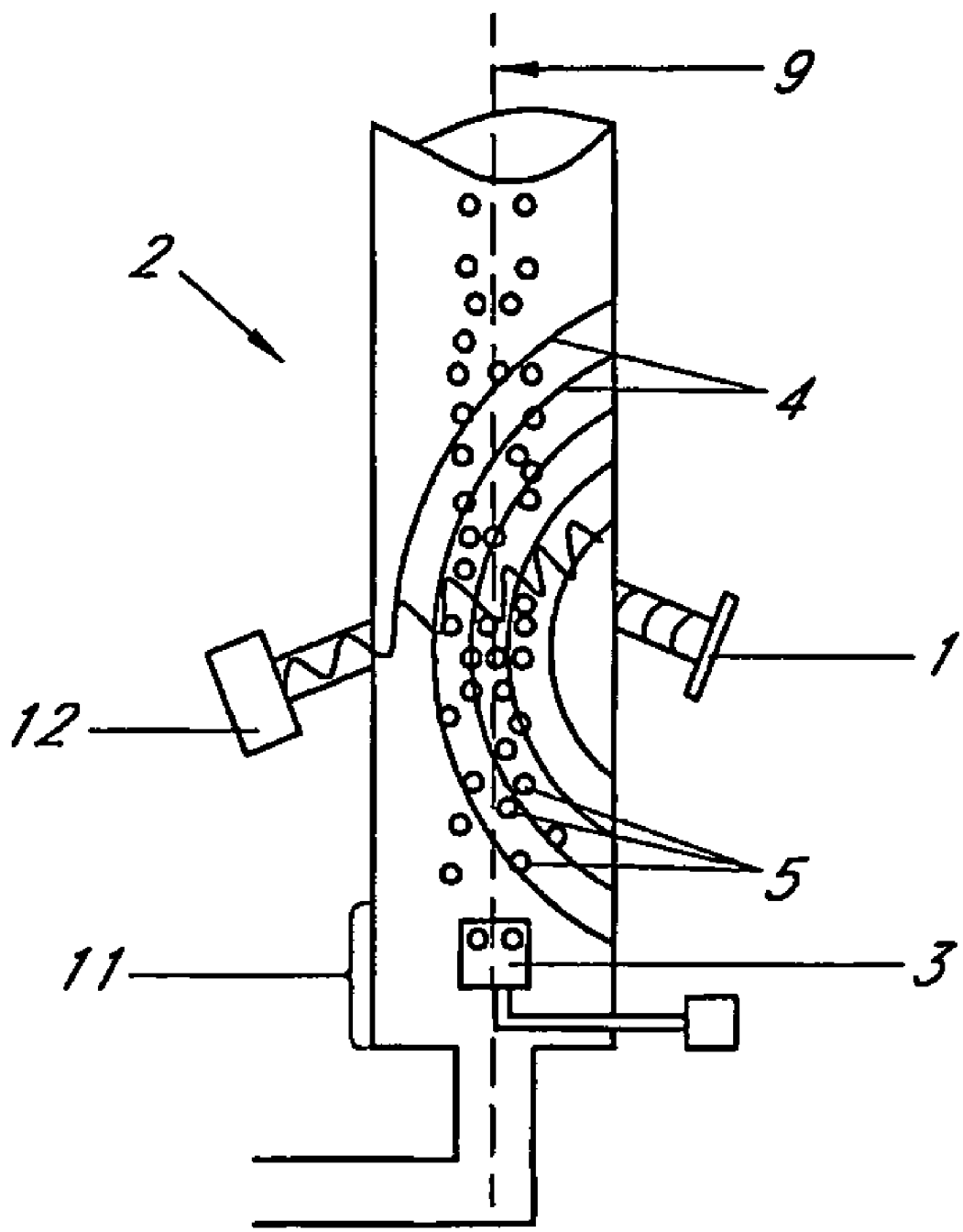
FIG. 1 is a drawing showing one embodiment of an ultrasonic treatment device described herein.

Embodiments of the devices that can be used to implement the inventive methods can be found in U.S. Provisional Application 60/423,368, U.S. application Ser. No. 10/358,445, and U.S. Pat. No. 6,540,922 to Cordemans et al., each of which are expressly incorporated herein by reference in their entireties. Methods of treating hyperproliferative cells can be performed with the devices disclosed herein. One particular embodiment of a device that can be used for treating a liquid medium such as an aqueous medium (e.g., physiological fluids) is illustrated in FIG. 1. In certain embodiments the fluids to be treated contain hyperproliferative cells. In other embodiments, the fluids to be treated can be a physiological liquid suspected of containing hyperproliferative cells, such as after diagnosis, for example. Cells which are not completely differentiated such as stem cells, as well as solutions containing viruses and/or virus infected cells can also be treated. Examples of treatable viruses can include HIV, HCV, HBV, Herpes virus, hantavirus, influenza, and Ebola, for example.

Referring to FIG. 1, the devices described herein include a compartment 2, preferably in the shape of a cylinder or a rectangular cross-section. In certain embodiments the compartment 2 can be in communication with a reservoir (not shown) which holds the liquid medium to be treated. In other embodiments (eg., when a human or animal physiological fluid is treated), the devices provided herein do not contain a reservoir that is directly connected to the human or animal body. Such embodiments include those wherein the physiological fluid is extracted and/or administered (e.g, reinjection) during extracorporeal treatment of the human or other animal body. Accordingly, an animal such as a human can be substituted for any reference herein to a "reservoir."

Figure 2:
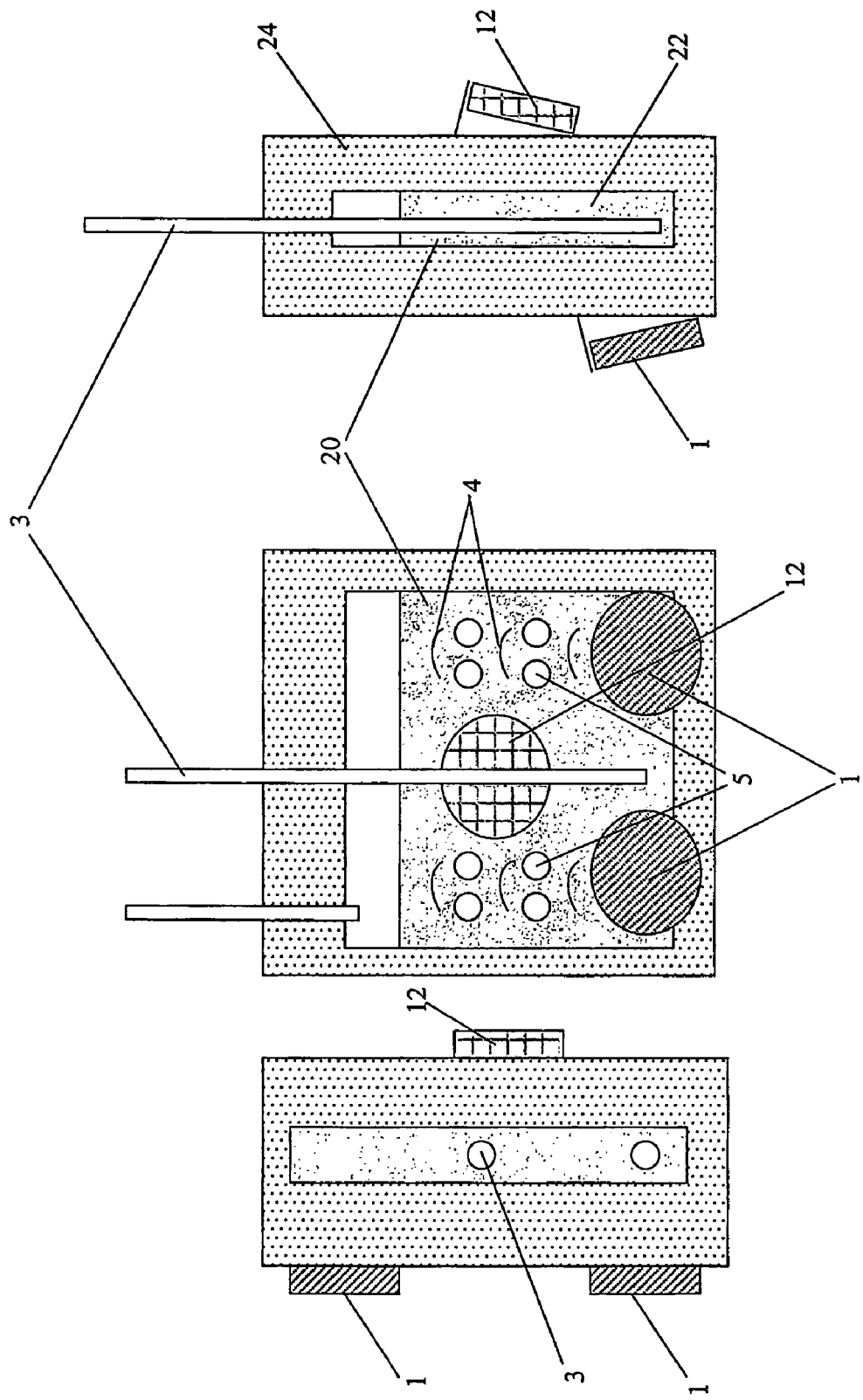
FIG. 2 is a drawing showing three views of an apparatus for treating hyperproliferative cells in a suspension with ultrasound and microbubbles. The far left view is an upper view of the apparatus, the middle view is a front view, and the far right view is a lateral view of the apparatus.

In other embodiments, a hyperproliferative cell suspension can be treated in a device as shown in FIG. 2. In this embodiment, an air inlet tube 3 is used as a microbubble emitter 3 to emit microbubbles 5 into the hyperproliferative cell suspension 22 contained in a compartment (or poach) 20. The compartment (or poach) 20 containing the cell suspension 22 may be immersed in a water bath 24, such as an incubator, for example.

In further embodiments, the compartment 2 contains (e.g., along its wall or adjacent to the bottom) one or more high-frequency ultrasound emitters 1 that emit ultrasound 4 into the compartment 2 (advantageously toward the center of this compartment 2). In other embodiments the container can also have one or more microbubble emitters 3 for emitting gas microbubbles 5, which are arranged so as to emit the gas microbubbles 5 into the ultrasound 4 field emitted in the compartment 20.

The term "microbubbles," as used herein is intended to refer to gas bubbles with an average diameter of less than 1 mm. In some embodiments, the diameter is less than or equal to 50 μm Still in other embodiments, the microbubbles have a diameter less than 30 μm. In certain embodiments the microbubbles are selected from air, oxygen, and ozone microbubbles or a mixture thereof. To lower operating costs, it can be advantageous to use microbubbles that are not ozone microbubbles, such as air microbubbles. Advantageous embodiments of the invention do not rely on the generation of a thermal effect to treat cells. While in certain embodiments the use of stabilized microbubbles can be effective in treating cells, in preferred embodiments, the use of stabilized microbubbles is unnecessary. Lipid boundary microbubbles are an example of a stabilized microbubble.

The term "hyperproliferative cells" is intended to refer to cells that divide, reproduce, or otherwise proliferate at a relatively high rate, and can include cancer cells (e.g., leukemic cells), precancerous cells, tumor cells, bone marrow cells, and totipotent cells.

In certain embodiments, the term "liquid medium" relates to physiological liquids which may be administered to man or animals, and/or extracted from man or animals. In specific embodiments, physiological fluids are reinjected after treatment (eg., an ex vivo treatment). In certain embodiments the term "physiological liquids" can include, without limitation, blood, serum, cephalorachidian, cerebrospinal fluid, plasma, and the like. U.S. Pat. No. 5,401,237, issued to Tachibana et al., describes a process of extracting and readministering physiological fluid, and is hereby expressly incorporated by reference in its entirety.

In specific embodiments, the methods and devices herein include low energy, high-frequency ultrasound to treat hyperproliferative cells. The term "high frequency" is intended to refer to frequencies greater than 100 kHz and up to several MHz. In certain embodiments, the high frequencies used are between 200 kHz and 20 MHz. In various embodiments, the ultrasound frequency can be selected from between 200 kHz to 10 MHz. In a preferred embodiment, the frequency used is between 200 kHz and 1.8 MHz.

In various embodiments of the devices described herein, the microbubble emitter 3 for emitting gas microbubbles 5 is arranged at the base 11 of the compartment 2, (i.e., at the bottom of the compartment 2), such that the microbubbles move by rising naturally or by entrainment of the gas in the flow of liquid.

In further embodiments, the devices and methods described herein induce apoptosis in hyperproliferative cells. It has been discovered that healthy cells are much less sensitive to high-frequency ultrasound than leukemic cells. This difference in behavior between the healthy and leukemic cells cannot be related to a difference in the localization of the endogenous photosensitizers but is probably due to a modification of the fundamental cell mechanisms such as p53 status, signaling pathways, and resistance to oxidative stress, for example. Specifically, apoptosis can be induced in cancerous cells (e.g., leukemic), precancerous cells, tumor cells, bone marrow cells, totipotent cells, and the like.

Although the present teachings are in no way to be limited by their precise mechanism of action, in more specific embodiments the devices and methods provided herein can produce radicals such as ROS (reactive oxygen species), H, OH and HOO which can also form $H_2O_2$, this molecule and/or these radicals being toxic to hyperproliferative cells and thus bring about their inactivation and/or destruction. Lipid peroxydation products, resulting from the oxidative stress created under the ultrasonic conditions are also potential participants to this biomechanism.

While evidence against singlet oxygen formation during sonodynamic therapy has been presented, these data are only consistent with a long and "high-energy" ultrasound exposure, leading to an accumulation of sensitizer-derived free radicals either by direct pyrolysis or due to reactions with H or OH radicals formed by pyrolysis of the water solvent.

The species created using the disclosed methods and devices are thought to be derived from the reaction of high-frequency ultrasound on a water molecule, most likely giving rise (in particular in the presence of oxygen) to the following reactions:

$$H_2L \rightarrow H+OH$$

$$H+O_2 \rightarrow HOO$$

$$HOO+HOO \rightarrow H_2O_2+O_2,$$

$$OH+OH \rightarrow H_2O_2$$

Advantageously, the energy required to produce these toxic species is reduced if the process is performed in the presence of microbubbles, as described herein. In certain embodiments, a generator is configured to supply power to the ultrasound emitter at less than 1 W/cm². In preferred embodiments, the power is supplied at about 0.5 W/cm² or lower, or more in many advantageous embodiments about 0.25 W/cm² or lower. In advantageous embodiments, the power dissipated in the volume of physiological fluid from this level of power applied to the emitter is less than 30 mW/cm³. In some embodiments, the power is dissipated at about 7 mW/cm³.

While in certain embodiments, the ultrasound can be administered continuously, in other embodiments, the ultrasound can be administered intermittently, using ON/OFF cycles. Those with skill in the art can determine effective ON/OFF cycle times depending on the volume of cells, type of cells, and other relevant variables.

In further embodiments the teachings herein relate to treating hyperproliferative cells in suspension, as opposed to a tumor or neoplastic mass. In these embodiments, the teachings herein do not rely on microbubbles to concentrate or pool at a particular tumor site. This allows for the treatment of unwanted hyperproliferative cells that do not happen to be clumped together.

Another advantage of the methods and devices provided herein is that the hyperproliferative cells can be effectively treated in short periods of time. In specific embodiments, hyperproliferative cells can be treated in under 1 minute. In even more specific embodiments, the cells can be treated in under 30 seconds, including between 5-20 seconds, for example.

As known in the art, biophysical modes of ultrasonic action are classified as having either thermal, cavitational, or non-thermal and non-cavitational effects. It is important to note that using the above-described power ranges and short treatment times, significant fluid and/or cell heating is avoided such that little or no heat generated cell death occurs. As an example, treatments resulting in a non-thermal effect include treatments conducted at temperatures below 40° C., 35° C., and 30° C. The power levels are also such that cavitation does not occur to a significant extent, such that cell membrane injury due to the ultrasound is substantially avoided.

Under higher ultrasound powers, it has been recently appreciated that the injection of microbubbles into the ultrasound field gives rise to an increase in the phenomenon of sonoluminescence, by superposition of the microbubbles onto the cavitation bubbles induced by the ultrasound, the number of excited and toxic species can be multiplied. This phenomenon is observed on a macroscopic level when the ultrasound treatment is synergistically combined with the presence of microbubbles of suitable size.

In additional embodiments, the devices and methods provided herein have the advantage that there is no need to devote the ultrasound to specific zones, since it is observed that the treatment system functions by diffusing the products formed in situ (for example radicals and $H_2O_2$ formed) towards the reservoir 6 of the aqueous medium to be treated.

In further embodiments, the one or more ultrasound 4 emitters 1 in the devices described herein are oriented so as not to give rise to any standing-wave phenomena. For example, in certain embodiments, one or more ultrasound emitters can be oriented obliquely relative to the axis 9 of the compartment 2 (acute angle not perpendicular to this axis 9) and relative to the flow of liquid and to the flow of microbubbles 5 (see FIG. 1) This characteristic makes it possible for all the microbubbles 5 in the compartment 2 to be treated in a statistically identical manner, without creating stationary zones in the compartment 2.

The devices and methods herein can include emitting gas microbubbles with an average diameter of less than 1 mm into a high-frequency ultrasound field in the treated liquid medium. In some embodiments the diameter of the microbubbles is less than or equal to 50 μM. Still in other embodiments the microbubbles have a diameter less than 30 μm. In certain embodiments the microbubbles are selected from air, oxygen, and ozone microbubbles. In other embodiments the microbubbles are not ozone microbubbles.

According to other embodiments, the devices and methods described herein can include a light emitter 12 (i.e. an electromagnetic radiation emitter) which emits into the compartment 2 in the ultrasound 4 field, radiation, with a frequency that is mostly in the visible range. However, for certain applications, in order to remove certain specific hyperproliferative cells, it is advantageous to emit electromagnetic radiation with a frequency that is mostly non-visible, as ultraviolet radiation (e.g. UVA, UVB or UVC type), infrared, laser, microwaves, and the like.

It has recently been discovered, unexpectedly, that a treatment comprising the emission of microbubbles into the fields combined with ultrasound and optionally light radiation is particularly effective at inactivating and removing hyperproliferative cells present in a liquid medium, such as a physiological fluid. The phenomenon of luminescence can promote the production of extremely active oxygenated species such as the superoxide radical or singlet oxygen, which can result in a series of biochemical reactions that are extremely toxic for certain hyperproliferative cells. In advantageous embodiments, the radiation is emitted intermittently in ON/OFF cycles. In more specific embodiments the ON/OFF cycle can be about 5.5 ms/3 ms.

It is known that luminescence can take place in the presence of so-called sensitizing molecules (e.g., photosensitizers and sonosensitizers), so as to give rise to an anti-tumor action on certain cancer cells. Such molecules can include: porphyrins, chlorines, tetracyclines, methylene blue, fluorescein, acridine, rhodamine, and the like. These active agents can be injected into the organism or administered orally and subsequently activated by sonoluminescence. After activation, these agents can produce singlet oxygens which in turn plays a fundamental role, in particular in biochemical processes resulting from oxidative stress. Specifically, a singlet oxygen can oxidize the various cell components, such as the proteins, lipids, amino acids and nucleotides, for example.

In other embodiments, solid particles or solid surfaces can be used to synergize the luminescence and/or emission of radiation. These solids can include $TIO_2$, clays, and ceramics, for example.

Various embodiments are directed towards devices and methods which do not require additional chemical products such as photosensitizers and/or sonosensitizers to neutralize, prevent the growth of, and/or remove hyperproliferative cells from a physiological medium. It is not always necessary to add a photosensitizing or sonosensitizing agent to the liquid medium to be treated, since it has been unexpectedly observed that luminescence can be produced in situ on certain hyperproliferative cells (e.g, leukemic cells) present in physiological fluids (e.g., blood) already containing these photosensitizing molecules.

While the devices and methods provided herein can be used in conjunction with other drugs such as photosensitizers, sonosensitizers, chemotherapeutic agents, antibiotics, antiviral drugs, it is important to note that the effectiveness of the provided methods and devices in treating hyperproliferative cells is not dependent on the use of other chemicals, reagents, or drugs. Accordingly, the methods and devices described herein can be used without additional substances, including chemicals, reagents, hormones, peptides, proteins, nucleic acids, carbohydrates, DNA vaccines, angiogenesis stimulators or drugs. In even more specific embodiments, the teachings herein do not rely on the cellular absorption of these substances.

Specifically, the effects obtained with the teachings herein can be achieved without the necessity of classical photosensitizers and sonosensitizers. The physiological effects obtained with techniques such as PDT depend at the same time on the radiation dose, on the nature of the photosensitizer used, on their concentration, and on their localization. While being requirements for traditional treatments, sensitizers are not needed for the teachings provided herein, thereby considerably simplifying the methods and devices.

In certain embodiments, the net effects of the ultrasonic action implicate endogenous photosensitizers in the structure where their local concentration is high. For example, endogenous photosensitizers are localized mainly in the membrane structures such as lysosomes, mitochondria, nuclear membranes, Golgi apparatus, and the microsomes of the endoplasmic reticulum, of which the relative surface represents nearly 50% of the cell membrane surface.

In some embodiments, the devices and methods described herein can include a pump for circulating the liquid medium, as well as one or more apparatuses for recovering, preferably by filtration, centrifugation or precipitation (such as cyclones, etc.), hyperproliferative cells present in the liquid medium. In certain embodiments the pump and/or apparatus for recovery are arranged between the reservoir (or animal) containing the liquid medium to be treated and the compartment 2.

In certain embodiments the devices and methods herein can be used to extract physiological fluid (e.g., blood) from a subject, suspected of (e.g., diagnosed) having cancer (e.g., leukemia). After extraction, the physiological fluid can be treated with high-frequency, low-energy ultrasound and gas microbubbles with diameters less than 1 mm. In certain embodiments the methods induce apoptosis on the cancerous cells (e.g., leukemia). After treating the physiological fluid such that the hyperproliferative cells have been either sufficiently neutralized, prevented from growing, or removed, the fluid can then be administered back to the subject. These methods can be performed similar to other ex vivo methods, such as hemodialysis, for example.

A blood treatment subject can be attached to one of the devices described herein. According to certain embodiments, the bloodstream of the subject can be connected to a ultrasound device described herein, through an internal fistula in their arm. This involves having an artery and a vein connected surgically. When they are joined, the stronger blood flow from the artery causes the vein to become larger. Needles can be inserted in the enlarged vein to connect the subject to the ultrasound device.

Another way to provide access to the bloodstream is to insert an internal graft. In this procedure an artery is surgically connected to a vein with a short piece of special tubing placed under the skin, which a needle can be inserted into.

In other embodiments, when it is necessary to gain access to the bloodstream quickly, or when the veins in the arms are too small to provide enough blood for ultrasonic treatment for example, a central venous catheter can be used. In this procedure, a soft tube is surgically inserted into a large vein in the neck or near the collarbone. In some embodiments this method can be temporary until a permanent access site is ready.

Subjects that can be treated according to the methods described herein can include any animal, such as a mammal, including humans, mice, monkeys, dogs, pigs and the like.

In further embodiments, the devices and methods herein utilize low-energy, high-frequency ultrasonic waves to prevent, treat, or neutralize hyperproliferative cells by inducing apoptosis in the cells (e.g. leukemic cells). Inducing apoptosis in hyperproliferative cells can lead to a sequence of characteristic events including a drop in mitochondrial potential, loss of phosphatidylserine asymmetry, morphological variations, DNA fragmentation, loss of plasma membrane, and the like. Furthermore, low-energy ultrasound-induced apoptosis can involve activation of caspase-3, the proteolytic degradation of the caspase substrate PARP, and the modulation of bcl-2/bax ratio in the cells.

Additional methods involve initiating apoptosis using ultrasound-induced sonochemical luminescence to trigger photosensitized singlet oxygen production from direct photoirradiation. In classic ultrasonic irradiation conditions, the direct destructive cavitation effects dominate the sonoluminescence, which is fairly weak in the absence of an air/liquid interface injected into the medium. Accordingly, it can be advantageous to utilize microbubbles in conjunction with ultrasound in order to enhance luminescence over cavitational effects.

The following examples describe treating cells with high-frequency, low-energy ultrasound and various assays to indicate the presence of apoptosis in said cells.

EXAMPLE 1

Cell Preparation and High-frequency Ultrasound Treatment

Human leukemia cell lines (K562, Nalm-6, KG1a, and HL-60) obtained from the American Type Culture Collection (ATCC, Rockville, Md., USA) were grown in RPMI-1640 (BioWhittaker, Walkersville, Md., USA) supplemented with 10% fetal calf serum (Gibco, Grand Island, N.Y., USA) and 1% L-glutamine (Gibco). Leukemic cells were harvested, resuspended in phosphate-buffered saline (PBS, pH=7.2, Gibco), and immediately used for the experiment. Heparinized venous blood was obtained from healthy volunteers and leukemic patients. Mononuclear cells were separated by Ficoll-Hypaque gradient density centrifugation (International Medical Products, Brussels, Belgium).

The following describes the ultrasonic treatment on the cells. Human leukemia cell lines (K562, HL-60, KG1a, and Nalm-6), primary leukemic cells, and normal mononuclear cells were treated by ultrasound at a frequency of 1.8 MHz during various exposure times at an acoustical power of 7 mW/mL and irradiation (ON/OFF) cycles of 5.5 ms/3 ms.

After 18 hours culture in the incubator (37° C. and 5% $CO_2$) the cells were successfully tested for cell viability by a trypan blue exclusion assay. Additional tests were performed on the treated cells and are described in more details in the following examples. Apoptosis was evaluated by cell morphology, phosphatidylserine exposure, and DNA fragmentation. The mitochondrial potential, glutathione content, caspase-3 activation, PARP cleavage, and bcl-2/bax ratio were tested by flow cytometry. Cloning efficiency was evaluated by assays in methylcellulose.

EXAMPLE 2

Effect of High-frequency Ultrasound on DNA Fragmentation

DNA fragmentation has been associated with apoptosis. Quantification of cells with degraded DNA was performed using a method described by Nicoletti, I. et al. *J Immunol Methods* 139(2):271 (1991) and an Apotarget Quick DNA Ladder Detection Kit (Biosource). Cell pellets (106 cells) were resuspended in 20 L of lysis buffer and DNA was extracted according to the manufacturer's instructions. DNA was analyzed after separation by gel electrophoresis (1% agarose). As a positive control, cells were irradiated with UV light by placing a plate directly under a UV transilluminator for 10 minutes (intensity of 5 mW/cm2). Cells were then incubated at 37° C. for 5 and 18 hours before apoptosis was assessed.

After permeabilization, cells were incubated with solution containing PI and RNAse (Coulter DNA-prep Reagent). The tubes were placed at 4° C. in the dark overnight before analysis by flow cytometry to identify the sub-G0 peak corresponding to apoptosis.

Classic nucleosomal DNA ladder patterns were observed in DNA samples from cells treated by ultraviolet (positive control) and by ultrasound. Internucleosomal DNA cleavage was barely noticeable 5 hours after the ultrasonic treatment but became clearly evident 18 hours afterwards (results not shown). Furthermore, an increase in the number of nuclei with fragmented DNA was observed with PI staining, 5 hours after treatment. Specifically, 15% of the treated cells had fragmented DNA and 2% of the untreated cells had fragmented DNA (data not shown).

EXAMPLE 3

Effect of High-frequency Ultrasound on Mitochondrial Transmembrane Potential

The early disruption of mitochondrial transmembrane potential ($\Delta Ym$), preceding advanced DNA fragmentation, has been observed in several models of cell apoptosis. The following assay was performed to determine the effect of high-frequency ultrasonic treatment on $\Delta Ym$.

Mitochondrial potential was estimated by incorporation of the cationic fluorocbrome DiOC6 immediately after cell treatment according to the published protocol found in A. Macho, et al., *Blood* 86(7):2481 (1995).

Briefly, K562 cells (106/mL) were incubated with 2.5 nmol/L 3,3'-dihexyloxacarbocyanine (DiOC6; Molecular Probes, Eugene, Oreg.) for 15 minutes at 37° C., followed by flow cytometric analysis.

Ultrasonic treatment was accompanied by an increase of cell populations displaying a low $\Delta Ym$ (results not provided). A population of cells displaying a reduced DiOC6 incorporation was evidenced 30 minutes after treatment, and the drop of mitochondrial potential was very clear 5 hours after the ultrasonic treatment with more than 50% of the cells having a low $\Delta Ym$. These results provide evidence of cellular apoptosis.

EXAMPLE 4

Effect of High-frequency Ultrasound on Cellular Glutathione Levels

It has been shown that there is a depletion of glutathione during apoptosis. An assay was performed to determine cellular glutathione content after ultrasonic treatment. Cell Tracker green CMFDA (5-chloromethyl fluorescein diacetate; Molecular Probes) was used for determining levels of intracellular glutathione as previously described in D. W. Hedley et al. *Cytometry* 15:349 (1994).

Figure 3:
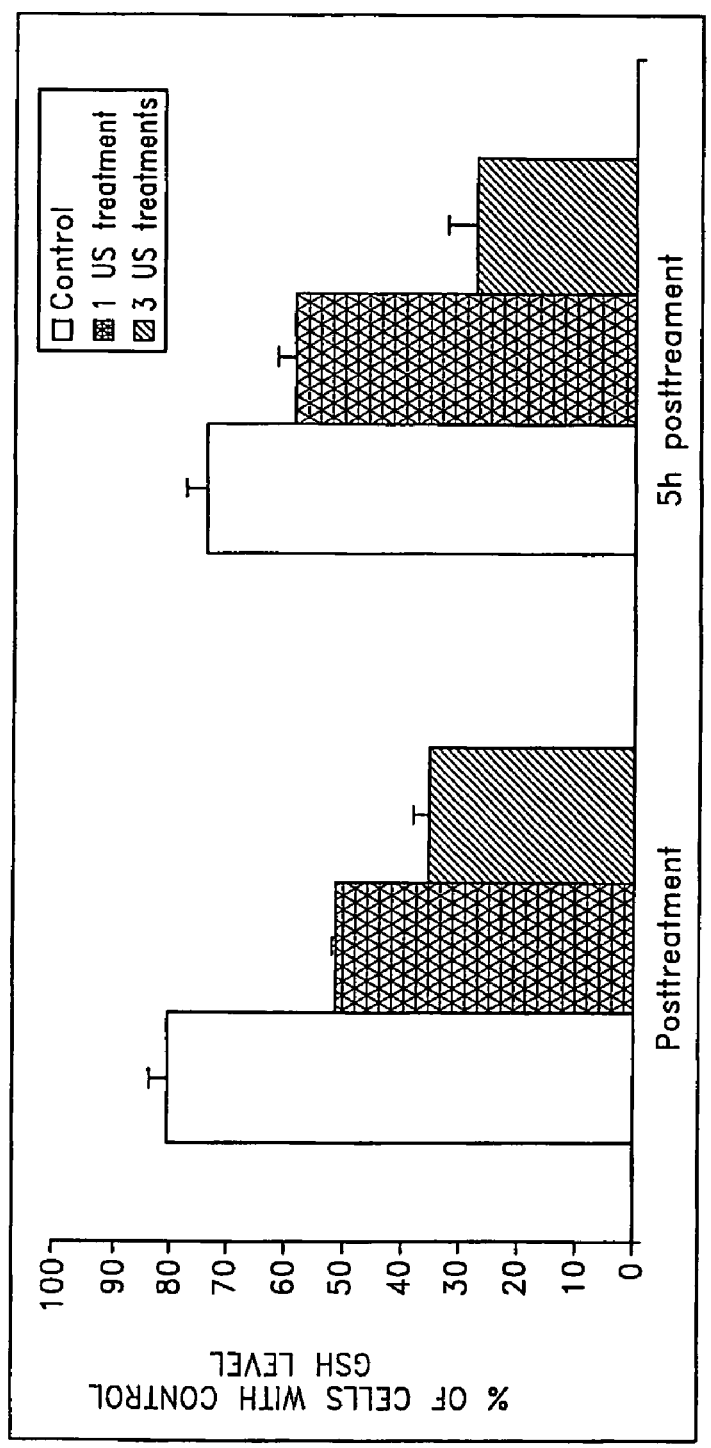
FIG. 3 is a bar graph showing the effects of ultrasonic treatment on cellular glutathione levels. Data are expressed in percentage of cells displaying glutathione level comparable to untreated cells. Values are mean ±SEM of 3 independent experiments.

Directly after ultrasonic treatment, a subpopulation appeared with lower levels of GSH than that observed in untreated cells (>50% of cells displaying a low level of GSH) as shown in FIG. 3. The results of successive treatments indicated a larger GSH depletion after 5 hours. The results, expressed as a percentage of cells displaying a GSH level comparable to untreated cells, clearly demonstrate that high-frequency ultrasonic treatment is associated with GSH depletion.

EXAMPLE 5

Effect of High-frequency Ultrasound on Cellular Caspase-3 Activity

Caspase-3 has been shown to play an important role in chemotherapy-induced apoptosis. Specifically, activation of caspases leads to cell demise via cleavage of cellular substrates such as actin, gelsolin, or PARP. To directly address the involvement of caspase-3 in ultrasound-induced apoptosis, caspase activity was determined using flow cytometry and calorimetric assay.

Specifically, caspase-3 was detected by flow cytometric analysis using the phycoerythrin (PE)-conjugated polyclonal rabbit antibody anti-active caspase-3 monoclonal antibody (BD-Pharmingen, San Diego, Calif., USA). Cells were fixed and permeabilized using Fix and Perm kit (Caltag, Burlingame, Calif.) for 15 minutes at room temperature. Cells were then stained with anti-caspase-3 Ab and incubated for 15 minutes. Cells were washed and analyzed by flow cytometry. The enzymatic activity of caspase-3 was determined using the Apotarget caspase-3/cpp32/colorinetric protease assay kit (Biosource), as suggested by the manufacturer. Caspase-3 activation was also indirectly evaluated by PARP cleavage using a rabbit anti-PARP cleavage site AB, FITC conjugate (Biosource).

Figure 4:
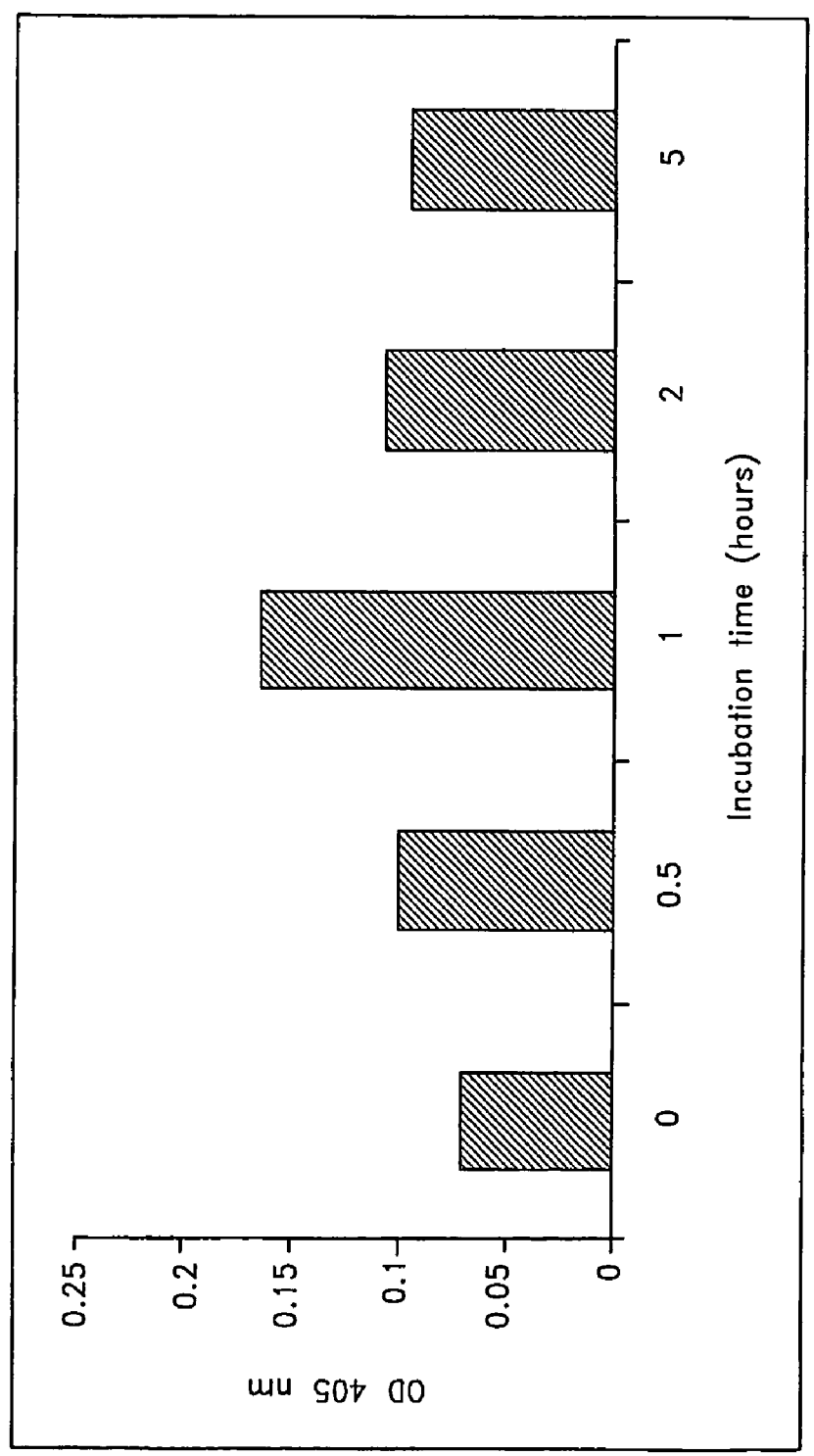
FIG. 4 is a bar graph representing the effects of high-frequency ultrasound on cellular caspase-3 activity.

As shown in FIG. 4, high-frequency ultrasonic treatment led to the activation of caspase-3. Moreover, this protease activity was maximal at 1 hour post-treatment. Furthermore, cleavage of PARP was apparent 2 hours after treatment, with 40% of cells stained by the rabbit anti-PARP FITC vs 5% for untreated cells (results not shown).

EXAMPLE 6

Effect of High-frequency Ultrasound on Cellular BCL-2/BAX Ratio

Different proteins of the bcl-2 family have been implicated in triggering or preventing apoptosis. The following assay was performed to determine whether bcl-2 and bax, the two major members of the bcl-2 family, were involved in the induction of apoptosis by ultrasound. After permeabilization, cells were incubated with isotype-matched negative control, FITC-labeled mouse anti-human bcl-2 (Dako, Glostrup, Denmark), and polyclonal rabbit antibodies to bax. Subsequently, a FITC-labeled secondary antibody (Dako) was added to bax. To quantify bcl-2 and bax expression, the cytometer was calibrated using a mixture of beads labeled with known amounts of fluorochrome (Dako). The values of mean fluorescent intensity (MFI) were then converted to molecules of equivalent soluble fluorochrome (MESF) using a calibration curve.

The results (data not provided) demonstrated that untreated cells expressed high levels of the anti-apoptotic protein-bcl-2 protein ($47\pm4\times103$ MESF) and this expression appears as a unimodal peak of fluorescence. One hour after ultrasonic treatment, the expression of bcl-2 protein was already down-regulated (respectively $40\pm0.9$ and $32\pm0.9\times103$ MESF in K562 cells treated by 1 or 3 ultrasonic treatments). Two hours after treatment, bcl-2 expression appeared clearly bimodal, the cells displaying either a bcl-2high (comparable to untreated cells) or bcl-2low phenotype ($11\pm2\times103$ MESF).

In contrast to bcl-2, levels of the pro-apoptotic protein, bax, were higher in cells treated with ultrasound as compared with untreated cells (respectively 85635 0.5 and 48·.·5×103 MESF for treated and untreated K562). The ratio of bcl-2/bax was thus significantly reduced during high-frequency ultrasonic treatment, providing evidence of cellular apoptosis (0.98 for control cells vs 0.38 for ultrasound-treated cells).

EXAMPLE 7

Effect of High-frequency Ultrasound on Levels of Cellular Phosphatidylserine

During apoptosis, phosphatidylserine residues flip from the inside to the outside of the plasma membrane and this change can be detected using Annexin-FITC, which binds to the PS residues. The following describes an Annexin V binding assay that was performed. Flow cytometric analysis of Annexin-V-fluorescein isothiocyanate (FITC)-and propidium iodide (PI)-stained cells was performed using the kit purchased from Biosource International (Camarillo, Calif., USA) as recommended by the manufacturer. Data were presented as dot plots showing the change in mean fluorescence intensity of Annexin-V-FITC/propidium iodide (not shown).

The results indicated that the changes of phosphatidylserine distribution varied according to time. Specifically, the results showed that ultrasonic treatment provoked plasma membrane injury in a low percentage of cells, demonstrating that the necrotic action of the tested ultrasound treatment is very weak. interestingly, an increase in apoptotic cells was observed two hours after treatment Five hours after the treatment, 35% of cells were Annexin-V-positive, demonstrating the ultrasonic induction of apoptosis in K562 cells.

EXAMPLE 8

Effect of High-frequency Ultrasound on Colony Formation

Figure 5:
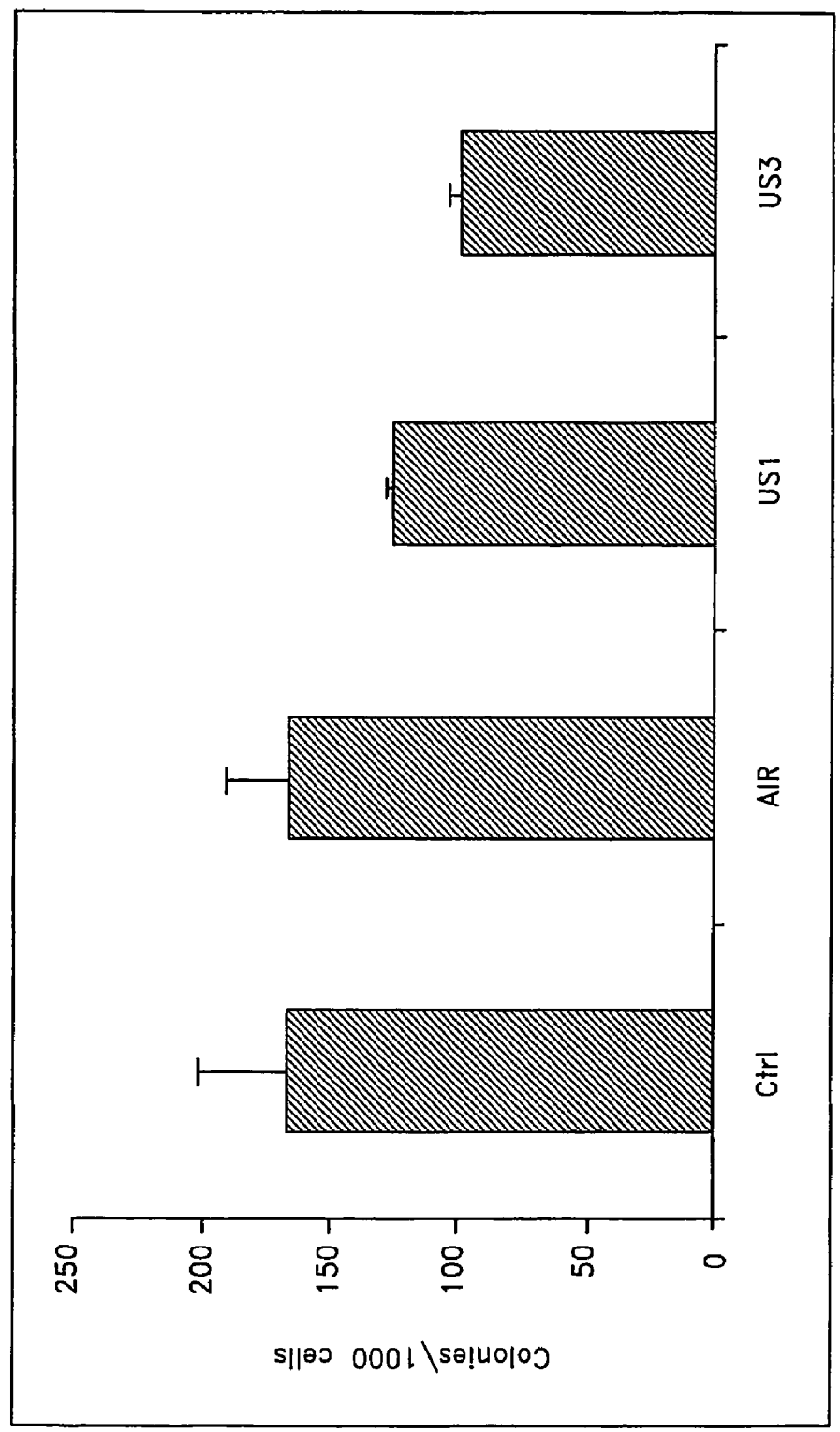
FIG. 5 is a bar graph showing the effect of irradiation on cloning efficiency of K562 cells. The results are expressed as mean ±SEM of 3 independent experiments.

An important proof for an effect on cell viability is the inability of a cell to multiply and form a colony. The following describes a clonogenic assay that was performed on a K562 cell line to determine the effect of high-frequency ultrasonic irradiation on cloning efficiency. Briefly, the culture medium consisted of IMDM supplemented with 20% FCS and methylcellulose at a final concentration of 4%. Cultures were incubated at 37° C. in 5% $CO_2$ air, and colonies (>20 cells) were scored after 5 days. The clonogenic efficiency of K562 cell line was 16%. As shown in FIG. 5, a significant reduction in cloning efficiency of K562 cells is observed after 1 and 3 treatments (respectively 25% and 42% of inhibition), confirming the sensitivity of leukemic cells to high-frequency ultrasound.

EXAMPLE 9

Effect of Oxygen Scavengers on Apoptosis

The following procedure was performed to determine the effect of active oxygen scavengers on the induction of apoptosis by high-frequency ultrasound. K562 cells were incubated with L-histidine (10 mM) and/or mannitol (100 mM). Some cells were treated by high-frequency ultrasound and others were not. Cell apoptosis was detected by an Annexin-V/PI assay. The results, as provided in Table 1, demonstrate that the ultrasonically induced cell damage is significantly reduced in the presence of histidine and mannitol (respectively 43% and 47% of inhibition of apoptosis induced by 3 successive treatments).

TABLE 1

Effects of active oxygen scavengers on ultrasonically induced cell apoptosis

|  | No US treatment | 1 US treatment | 3 US treatments |
|---|---|---|---|
| No agent | 18 ± 6 | 42 ± 8 | 63 ± 5 |
| Histidine | 15 ± 5 | 24 ± 8 | 36 ± 11 |
| Mannitol | 11 ± 4 | 21 ± 5 | 30 ± 3 |
| Histidine + Mannitol | 11 ± 2 | 16 ± 3 | 25 ± 5 |

Results are expressed as percentage of cells displaying phosphatidylserine externalization 5 hours post-treatment (mean ± SEM from 4 independent experiments).

The association of mannitol and histidine led to more than 60% of inhibition of apoptosis. The effectiveness of these agents on reducing cellular apoptosis induced by ultrasonic treatment provides evidence that ultrasonically induced singlet oxygen and hydroxyl radicals are important mediators to induce apoptosis.

EXAMPLE 10

Effect of Successive Treatments of High-frequency Ultrasound on Cells

Figure 6:
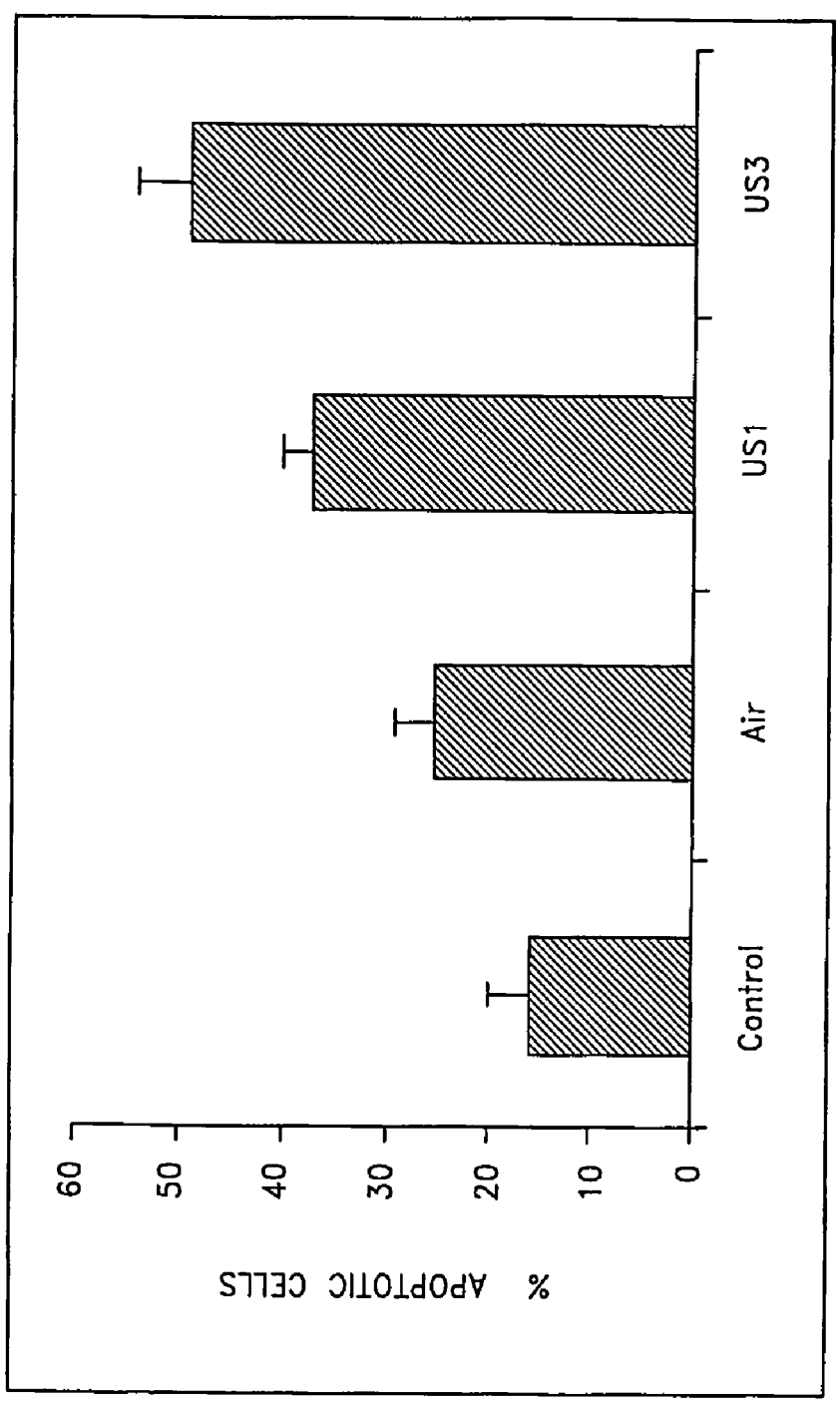
FIG. 6 is a bar graph showing the percentage of apoptotic K562 cells 5 hours after 1 or 3 ultrasonic treatments. The rate of apoptosis is determined by flow cytometry after Annexin-V staining and the results are expressed as mean ±SEM of 7 independent experiments.
Figure 7:
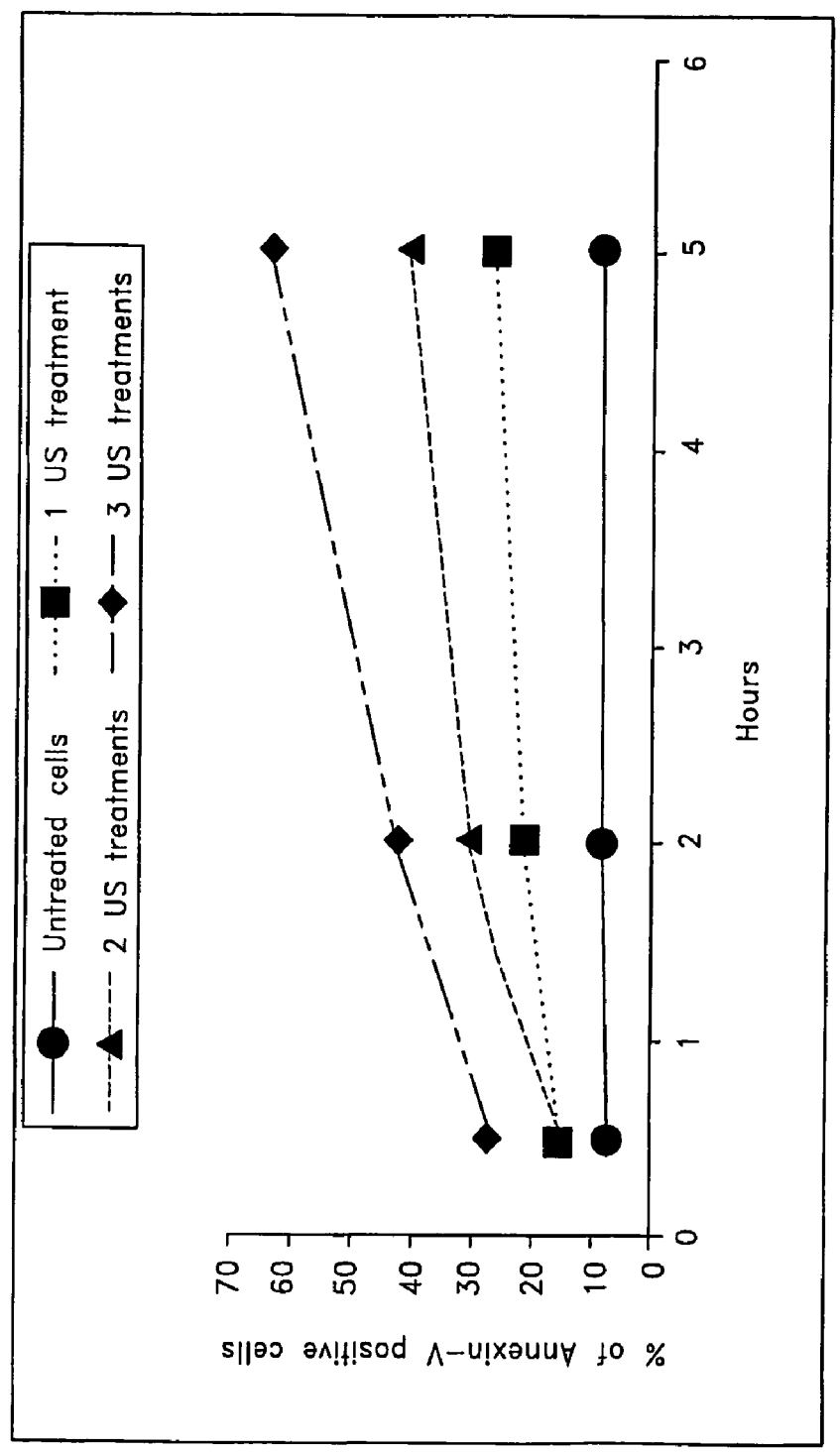
FIG. 7 is a point graph showing the changes of phosphatidylserine distribution according to time and successive ultrasonic treatments. Results from one representative experiment are expressed as percentage of cells stained with Annexin-V-FITC.

A flow cytometry follow-up was performed on K562 cells cultured 0.5, 2, and 5 hours after ultrasonic treatment. After one treatment, the level of apoptotic cells observed was three times that of the control (respectively 26% and 8% after 5 hours of culture for treated and untreated cells). A necrotic effect of 5 to 10% was also observed, which is well below that found when using drugs or photodynamic treatment (PDT) treatment. With successive irradiations, under the same conditions (7 mW/mL, 20 seconds) and at different intervals, apoptosis of K562 cells increased to 37±3% ($p<0.02$) and 49±5% ($p<0.02$) after respectively 1 and 3 successive treatments (FIG. 6). Morphological variations (e.g. cell shrinkage, membrane blebbing, chromatin condensation) were also observed after successive treatments (results not shown). FIG. 7 demonstrates that the amount of cellular phosphatidylserine increases after successive high-frequency ultrasound treatments as detected by an Annexin-V assay.

EXAMPLE 11

Effect of High-frequency Ultrasound on Various Cell Lines

Figure 8:
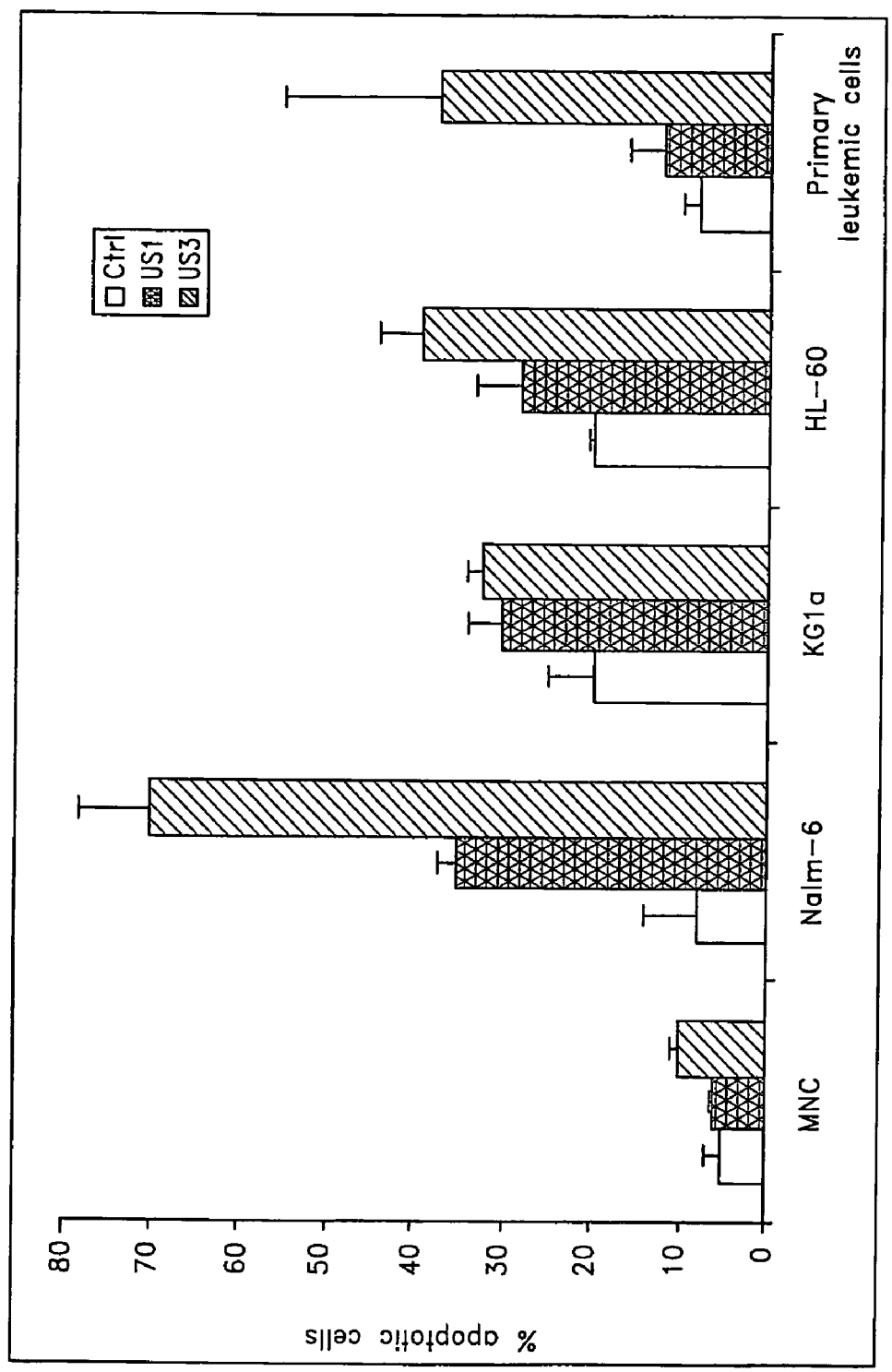
FIG. 8 is a bar graph showing the effect of ultrasonic treatment on the apoptosis of normal mononuclear cells (MNC and leukemic cells (Nalm-6, KG1a, HL-60, and primary leukemic cells obtained from 5 patients). Results are mean ±SEM of 5 independent experiments.

In addition to K562, the effect of ultrasonic treatment was tested on other normal and malignant cell lines, including KG1a (immature minimally differentiated acute myeloid leukemia blasts), HL-60 (promyelocytic leukemia), and Nalm-6 (ALL cell line). The results presented in FIG. 8 demonstrate that the sensitivity to ultrasound depends on cell type, but successive treatments led to a significant increase in the number of apoptotic cells for all cell lines evaluated.

Mononuclear cells from 5 patients (1 refractory anemia with excess of blast cells [RAEB], 1 secondary acute myelogenous leukemia [AML], and 3 cases of AML French-American-British [FAB] classification M3, M4, and M4Eo) were also treated by ultrasound, and blast cells were discriminated from contaminating normal cells on the basis of their CD45 expression as previously described in F. Lacombe, F. et al. *Leukemia* 11:1878 (1997). These cells had also been labeled for their phosphatidylserine exposure by FITC-annexin. This method makes it possible to compare the respective apoptotic behavior of leukemic blast cells and normal cells treated by ultrasound. The results presented in FIG. 8 demonstrate that primary leukemic cells are sensitive to ultrasonic treatment with more than 37±18% of apoptotic cells observed 5 hours after 3 treatments.

The foregoing description details certain embodiments of the teachings herein. It will be appreciated, however, that no matter how detailed the foregoing appears in text, the devices and methods herein can be practiced in many ways. As is also stated above, it should be noted that the use of particular terminology when describing certain features or aspects of the teachings herein should not be taken to imply that the terminology is being re-defined herein to be restricted to including any specific characteristics of the features or aspects of the teachings herein with which that terminology is associated. The scope of the teachings herein should therefore be construed in accordance with the appended claims and any equivalents thereof.

What is claimed is:

1. A method of neutralizing, removing and/or preventing the growth of hyperproliferative undifferentiated, or virally infected cells suspended in a physiological fluid comprising:
   placing a compartment containing the physiological fluid in a water bath;
   emitting ultrasound having a frequency higher than 100 kHz into said water bath at a power level that is about 7 mW/cm$^3$, to emit an ultrasound field into said compartment; and
   emitting gas comprising microbubbles into the ultrasound field in the compartment containing the physiological fluid, such that the emission of ultrasound and gas bubbles induces significant programmed cell death in the hyperproliferative, undifferentiated, or virally infected cells without causing significant cavitation or significantly heating the fluid so as to maintain the temperature of the physiological fluid at less than 40 degrees C.

2. The method according to claim 1, wherein the microbubbles are not ozone bubbles.

3. The method according to claim 1, wherein the microbubbles are selected from the group consisting of air and oxygen bubbles.

4. The method according to claim 1, wherein the physiological fluid is administered to a mammal and/or extracted from a mammal.

5. The method according to claim 1, wherein the physiological fluid is selected from the group consisting of blood, plasma, serum and cerebrospinal fluid.

6. The method according to claim 1, wherein the average diameter of the microbubbles is less than 50 μm.

7. The method according to claim 1, wherein the average diameter of the gas microbubbles is less than 30 μm.

8. The method according to claim 1, wherein the ultrasound emitted into the compartment does not generate a stationary field phenomenon.

9. The method according to claim 1, further comprising emitting light having an electromagnetic radiation mainly in the visible range into the ultrasound field.

10. The method according to claim 1, wherein the hyperproliferative cells are selected from the group consisting of tumor cells, bone marrow cells, stem cancer cells, and pre-cancerous cells.

11. The method of claim 1, wherein the hyperproliferative cells are leukemic cells.

12. The method of claim 1, further comprising supplying power to the ultrasound emitter at less than 1 W/cm$^2$.

* * * * *